(12) United States Patent
De Oliveira Da Silva et al.

(10) Patent No.: US 12,577,366 B2

(45) Date of Patent: Mar. 17, 2026

(54) CATALYSTS AND METHOD FOR PRODUCING RECYCLED POLYESTER

(71) Applicants: PETRÓLEO BRASILEIRO S.A.—PETROBRAS, Rio de Janeiro (BR); UNIVERSIDADE FEDERAL DO RIO DE JANEIRO—UFRJ, Rio de Janeiro (BR); UNIVERSIDADE FEDERAL DE PERNAMBUCO—UFPE, Recife (BR)

(72) Inventors: Wellington De Oliveira Da Silva, Nova Iguaçu (BR); Stevie Hallen Lima, Rio de Janeiro (BR); Marcos Lopes Dias, Rio de Janeiro (BR); Lys Sirelle, Rio de Janeiro (BR); Jose Geraldo De Andrade Pacheco Filho, Rio de Janeiro (BR); Jacicleide Nascimento De Andrade, Rio de Janeiro (BR); Hezrom Saulo Do Nascimento Júnior, Rio de Janeiro (BR); Daniela Emilia Bastos Lopes, Rio de Janeiro (BR); Ana Paula Cipriano De Arcanjo, Rio de Janeiro (BR); Aline Machado De Castro, Rio de Janeiro (BR)

(73) Assignees: PETRÓLEO BRASILEIRO S.A.—PETROBRAS, Rio de Janeiro (BR); UNIVERSIDADE FEDERAL DO RIO DE JANEIRO—UFRJ, Rio de Janeiro (BR); UNIVERSIDADE FEDERAL DE PERNAMBUCO—UFPE, Recife (BR)

( * ) Notice: Subject to any disclaimer, the term of this patent is extended or adjusted under 35 U.S.C. 154(b) by 863 days.

(21) Appl. No.: 17/275,856

(22) PCT Filed: Sep. 12, 2019

(86) PCT No.: PCT/BR2019/050392

§ 371 (c)(1),
(2) Date: Mar. 12, 2021

(87) PCT Pub. No.: WO2020/051665

PCT Pub. Date: Mar. 19, 2020

(65) Prior Publication Data

US 2022/0041836 A1 Feb. 10, 2022

(30) Foreign Application Priority Data

Sep. 12, 2018 (BR) ......................... 102018068454-0

(51) Int. Cl.
B01J 23/00 (2006.01)
B01J 23/06 (2006.01)
(Continued)

(52) U.S. Cl.
CPC ............. C08J 11/26 (2013.01); B01J 23/002 (2013.01); B01J 23/06 (2013.01); B01J 23/20 (2013.01);
(Continued)

(58) Field of Classification Search
CPC ........ C08J 11/26; C08J 2367/02; B01J 35/40; B01J 23/002; B01J 23/06; B01J 23/20;
(Continued)

(56) References Cited

U.S. PATENT DOCUMENTS 8,247,345 B2 * 8/2012 Shimizu ................. C08G 63/85
528/279
2010/0041913 A1 2/2010 Umaba et al.

FOREIGN PATENT DOCUMENTS

CN 105062074 A * 11/2015
EP 2184309 B1 6/2013
(Continued)

OTHER PUBLICATIONS

Pérez-Ramírez, Javier, et al. "On the stability of the thermally decomposed Co—Al hydrotalcite against retrotopotactic transformation." Materials research bulletin 36.10 (2001): 1767-1775.*
(Continued)

*Primary Examiner* — Richard M Rump

(74) *Attorney, Agent, or Firm* — Morrison & Foerster LLP

(57) ABSTRACT

The present invention describes the preparation of heterogeneous catalysts of mixed oxides based upon niobium and mixed oxides of zinc, manganese, nickel, cobalt and/or aluminum, originating from hydrotalcites (HTs) as precursor phase of heterogeneous catalysts, and application thereof in the chemical recycling of poly(ethylene terephthalate) (PET) for the production of metal free bis(hydroxy)ethylene (Continued)

(BHET) monomers and oligomers having a processing performance similar to that of the homogeneous catalysis system.

3 Claims, 8 Drawing Sheets

(51) Int. Cl.

| | |
|---|---|
| *B01J 23/20* | (2006.01) |
| *B01J 23/34* | (2006.01) |
| *B01J 23/75* | (2006.01) |
| *B01J 23/755* | (2006.01) |
| *B01J 23/889* | (2006.01) |
| *B01J 35/40* | (2024.01) |
| *C07C 67/02* | (2006.01) |
| *C08G 63/183* | (2006.01) |
| *C08J 11/26* | (2006.01) |

(52) U.S. Cl.
CPC .............. *B01J 23/34* (2013.01); *B01J 23/75* (2013.01); *B01J 23/755* (2013.01); *B01J 23/8892* (2013.01); *B01J 35/40* (2024.01); *C07C 67/02* (2013.01); *C08G 63/183* (2013.01); *C08J 2367/02* (2013.01)

(58) Field of Classification Search
CPC . B01J 23/34; B01J 23/75; B01J 23/755; B01J 23/8892; C07C 67/02; B08G 63/183
See application file for complete search history.

(56) References Cited

FOREIGN PATENT DOCUMENTS

| | | |
|---|---|---|
| WO | 2016096767 A1 | 6/2016 |
| WO | 2020051665 A1 | 3/2020 |

OTHER PUBLICATIONS

Allada, Rama kumar, et al. "Thermochemistry and aqueous solubilities of hydrotalcite-like solids." Science 296.5568 (2002): 721-723.*

Chen, Aimin, et al. "M—Mn—Al Hydrotalcite-like Compounds as Precursors for Methyl Benzoate Hydrogenation Catalysts." Industrial & engineering chemistry research 43.20 (2004): 6409-6415.*

Rackley, S. "Chapter 8—$CO_2$ adsorption". Negative Emissiosn Technologies for Climate Change Mitigation. 133-161 (2023).*

Intissar, Mourad, et al. "Trivalent cation substitution effect into layered double hydroxides $Co_2Fe_yAl_{1-y}(OH)_6CI-nH_2O$: study of the local order: ionic conductivity and magnetic properties." Journal of Solid State Chemistry 167.2 (2002): 508-516.*

Shao, Yuankai, et al. "The outstanding performance of LDH-derived mixed oxide Mn/CoAlO x for Hg 0 oxidation." Catalysis Science & Technology 5.7 (2015): 3536-3544.*

Stanimirova, T. S., et al. "Thermal decomposition products of hydrotalcite-like compounds: low-temperature metaphases." Journal of Materials Science 34 (1999): 4153-4161.*

El-Toufaili, Faissal-Ali, et al. "Studies on Hydrotalcite-Catalyzed Synthesis of Poly (ethylene terephthalate)." Macromolecular Materials and Engineering 291.9 (2006): 1136-1143.*

Chen et al. (Jun. 11, 2014). "Calcined Zn/Al Hydrotalcites as Solid Base Catalysts for Glycolysis of Poly(ethylene terephthalate)," Journal of Applied Polymer Science 131(22):41053 (10 pages).

* cited by examiner

CATALYSTS AND METHOD FOR PRODUCING RECYCLED POLYESTER

CROSS-REFERENCE TO RELATED APPLICATIONS

This application is a U.S. national phase filing under 35 U.S.C. § 371 of International Application No. PCT/BR2019/050392, filed Sep. 12, 2019 and claims priority to Brazilian Application No. PI 102018068454-0, filed Sep. 12, 2018. The entire contents of the prior applications are incorporated herein by reference in their entity.

FIELD OF THE INVENTION

The present invention relates to the production of recycled polyester employing heterogeneous catalysts. More specifically, the present invention relates to the preparation of heterogeneous catalysts of mixed oxides based upon niobium and mixed oxides of zinc, manganese, nickel, cobalt and/or aluminum originating from hydrotalcites (HTs) as precursor phase of heterogeneous catalysts, and the application thereof in the chemical recycling of poly(ethylene terephthalate) (PET) for the production of metal free monomers and oligomers of bis(hydroxy)ethylene (BHET) and having a processing performance similar to that of the system with homogenous catalysis.

BASIS OF THE INVENTION

Poly(ethylene terephthalate) (PET) is a product employed widely in the industrial manufacture of bottles and high strength fibers. As a consequence of this demand, at the present time the generation of post user PET has increased steeply worldwide, particularly by virtue of to the increase in demand for PET containers.

Furthermore, the petroleum industry utilizes this material on a large scale in ropes of large diameter manufactured from fibers of PET, these being withdrawn from use after some years of service generating, as a consequence, a large environmental liability.

Among the existing methods for the recycling of PET chemical recycling is advantageous, by virtue of the fact that it leads to the formation of raw materials utilized for the manufacture of PET, being in accordance with the principles of sustainable development. The catalysts traditionally used for the chemical recycling of PET are based upon metal acetates ($Zn^{+2}$, $Mn^{+2}$, $Co^{+2}$, $Pb^{+2}$), zinc acetate being that presenting greatest activity in the depolymerization of PET. However, the use of zinc acetate in this reaction presents the disadvantage of the reaction time required for the depolymerization of this polyester into the monomers and oligomers thereof, which may exceed 8 h of reaction. Nevertheless, this time may be reduced through maintaining the post user PET in contact with the ethylene glycol prior to the reaction of glycolysis.

Although the homogenous catalysts based upon zinc acetate bring about the complete conversion of PET into BHET in approximately 60 minutes of reaction, a great disadvantage is presented by the separation of this catalyst from the final product by virtue of the solubility thereof in ethylene glycol, this requiring additional separation processes. In addition, such homogenous catalysts are difficult to recycle and cannot be reutilized in a new process, and they can also affect the purity of the products generated.

In this context, heterogeneous catalysis arises as an alternative to the catalysts in existence in the state of the art, by virtue of the fact that the process of separation between the catalyst and the product becomes simple to execute when compared with the homogenous system. In addition thereto, the heterogeneous catalyst may be simply regenerated and subsequently reinserted into the plant in a new process of PET glycolysis. Furthermore, the BHET obtained from chemical recycling with homogenous catalysts may contain metals in concentrations incompatible with the use of the PET in the food industry.

Consequently, the development of a chemical PET recycling process and of heterogeneous catalysts suitable for this reaction having a processing performance similar to that of the homogenous catalysis system is shown to be fundamental for the production of BHET.

In this sense, the document CHEN F., et al., Calcined Zn/Al hydrotalcites as solid base catalysts for glycolysis of poly(ethylene terephthalate), *Journal of Applied Polymer Science,* 2014, 131, 41053, doi: 10.1002/app.41053, describes the glycolysis of PET utilizing catalysts of oxides obtained from hydrotalcites based upon Zn/Al. The catalysts proposed by this document present the disadvantage of requiring a high pH in the synthesis, together with heating to age the material prepared and a high calcination temperature. In addition thereto, the best catalysts obtained in this study present a low specific area and do not achieve 100% PET conversion, this possibly having been influenced through the utilization of precipitation reagents containing sodium in the composition thereof. Additionally, catalysts of the mixed Ni/Al oxide type were also tested, they presenting a low conversion of PET (15.7%) rendering the utilization thereof non-viable in the glycolysis reaction.

For its part, the document PRADO, R. M. K., et al., Short-time glycolysis of post-consumer PET catalyzed by different metal complexes, *Progress in Rubber, Plastics and Recycling Technology,* Vol. 24, No. 3, 2008, pp. 183-198, considers metal acetates and acetylacetonates as catalysts in the glycolysis of PET. The catalysts in this study are soluble in the glycolysis medium, permitting greater contact with the reagents and, consequently, facilitating the conversion. However, the removal thereof from the reaction medium prejudices the purity of the product formed and, furthermore, the catalyst cannot be reutilized in the process.

The document MARIANO, R. G. B., et al., Avaliação do Potencial de Catalisadores à Base de Nióbio em Reações de Glicólise do PET-Poli (Tereftalato de Etileno) [Evaluation of the potential of catalysts based upon niobium in glycolysis reactions of PET-poly(ethylene terephthalate], *XXVI Jornada de Iniciação Científica, Artística e Cultural,* Oral Presentation (Book of Abstracts, p. 164), reveals the use of niobium phosphate as glycolysis catalyst, applied to the glycolysis of propylene glycol. Despite it being a matter of a solid catalyst, it does not generate BHET. In addition thereto, there is no indication regarding the activity of the niobium phosphate as a glycolysis catalyst with ethylene glycol for the obtainment of BHET.

Flowing from the foregoing, there are no reports in the state of the art anticipating heterogeneous catalysts of mixed oxides based upon niobium and mixed oxides of zinc, manganese, nickel, cobalt and/or aluminum, originating from hydrotalcites (HTs) as precursor phase of heterogeneous catalysts, and nor of a process of chemical recycling of PET utilizing such catalysts for the production of metal free monomers and oligomers of BHET.

SUMMARY OF THE INVENTION

The present invention relates to heterogeneous catalysts of mixed oxides and the application thereof in the chemical recycling of PET for the production of monomers and oligomers of BHET.

A first object of the present invention is the preparation of mixed oxide catalysts based upon niobium and upon hydrotalcites as precursor phase of heterogeneous catalysts for the chemical recycling of PET, by glycolysis, having a performance similar to that of the homogenous system and having the objective of the obtainment of metal free monomers and oligomers of BHET.

A second object of the present invention is the realization of a process of production of metal free monomers and oligomers of BHET from the chemical recycling of PET under relatively gentle reaction conditions, with high catalytic activity, reutilizing the catalyst in the process of glycolysis, in this manner minimizing the processing costs in addition to generating value from PET residues with an alternative route for the proper fate for this material subsequent to its useful life.

In order to achieve the aforedescribed objects the present invention proposes the preparation of heterogeneous catalysts of mixed oxides based upon niobium and catalysts based upon hydrotalcites of mixed oxides of zinc, manganese, nickel, cobalt and/or aluminum having the objective of achieving high catalytic activity, lowest possible concentration of catalyst, and reutilization of the catalyst employed in the process.

The catalysts thus obtained would not interfere in any manner in subsequent processes of polymerization utilizing BHET as monomer, presenting, as additional advantages, simple separation and reutilization of the catalysts in the same process.

Such a process would render viable the separation and reutilization of the catalyst in the process and would also reduce the demand for p-xylene and purified terephthalic acid (PTA), in this manner reducing the processing cost and contributing towards the reduction in the emission of fossil carbon dioxide and in the consumption of energy, by virtue of a smaller number of processes for production of the PET.

For this reason, new methods for chemical recycling of PET for the generation of the monomer thereof, bis(hydroxy)ethylene terephthalate (BHET), would lead to technologically-interesting innovations from the environmental and strategic point of view for the polymer industry. As effects of this chemical recycling route in the PET manufacturing industry there may be cited:

(i) production of recycled PET having the characteristics of virgin PET in order to render viable the application thereof in the production of special industrial fibers without the risk of obtaining a fiber having reduced strength;

(ii) obtainment of a recycled PET having a purity equivalent to virgin PET for use in the food industry;

(iii) promotion of processing economy, by virtue of the fact that the principal input for the production of PET is the BHET originating from the glycolysis of the post user PET, resulting in a reduction in the demand for petroleum derivatives to produce para-xylene and purified terephthalic acid (PTA);

(iv) contribution towards the reduction in the emission of fossil carbon dioxide and reduction in the consumption of energy, by virtue of a smaller number of processes for production of the PET.

Consequently, the present invention may provide significant economy in the industry and, in addition, add greater value to the post user waste PET which previously might have been destined for mechanical recycling, incineration, or landfill.

These objects and other advantages of the present invention shall become clearer on the basis of the description below and the appended drawings.

BRIEF DESCRIPTION OF THE FIGURES

The detailed description presented below makes reference to the appended figures, wherein.

DETAILED DESCRIPTION OF THE INVENTION

Figure 1:
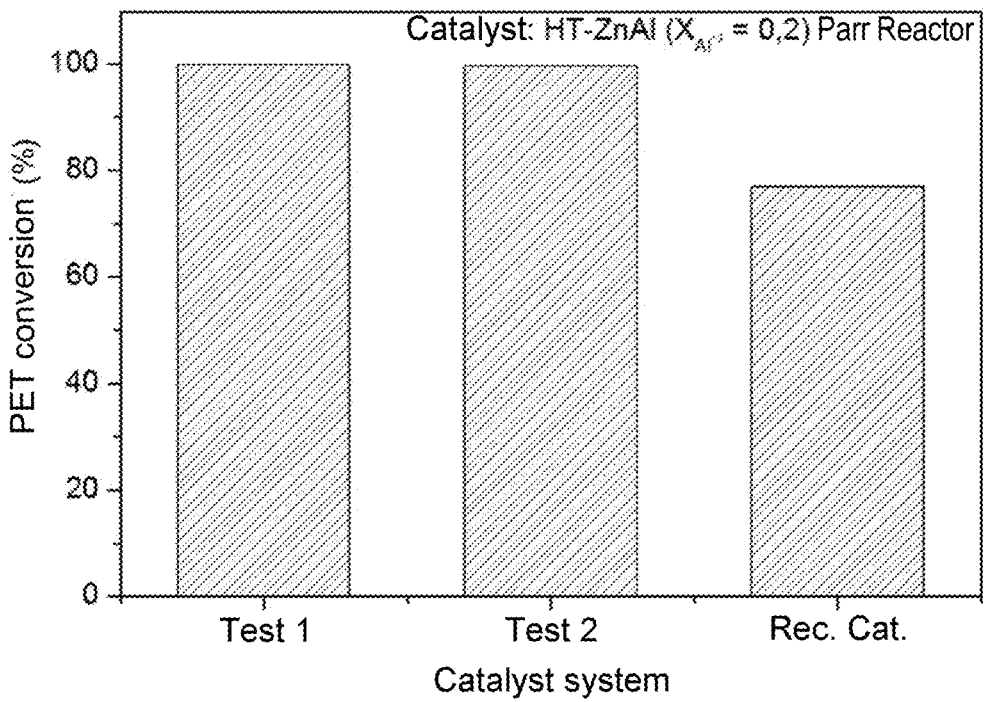
FIG. 1 represents the results of conversion of PET into BHET with ZnAl oxide catalyst.

The present invention relates to a process for the preparation of heterogeneous catalysts based upon mixed oxides and of laminar duplex hydroxides or hydrotalcites for the production of BHET monomers and/or oligomers from the recycling of polyester, together with the catalysts thus obtained.

The present invention furthermore relates to a process for the production of metal free monomeric and/or oligomeric crystalline BHET from recycled polyester, employing glycolysis technology utilizing the said catalysts.

Within the scope of the present invention, "recycling of polyester" is understood to be the recycling of any material based upon PET selected from the group consisting, inter alia, of textile fibers, films for adhesives, beverage containers, coated paper, mats, nonwoven blankets, cords, brooms, resins, clothing, footwear, suitcases, ropes, linings, coatings, textiles, tubes. Preferentially, the recycling of polyester is realized with materials selected from among post user PET containers and/or ropes of large diameters for offshore applications (made with PET fibers).

In one form of the present invention the heterogeneous catalysts are based upon mixed oxides derived from oxides of niobium with other metal oxides (preferentially zinc oxides) and of structures of laminar duplex hydroxides or hydrotalcites based upon zinc, manganese, nickel and/or aluminum with other hydroxides and salts.

Preferentially, the said catalyst is based upon the reaction of the salts of the metals zinc, manganese, nickel, cobalt and/or aluminum with other hydroxides and salts and preferentially obtained by the coprecipitation process, forming crystalline solids insoluble in aqueous solvents and ethylene glycol, having the general formulas (I) to (VIII), as follows:

$$Zn_{(1-x)}Al_x(OH)_2(CO_3)_{x/2}.mH_2O \qquad (I);$$

$$(Zn_{0.67}Mn_{0.33})_{(1-x)}Al_x(OH)_2(CO_3)_{x/2}.mH_2O \qquad (II);$$

$$Ni_{(1-x)}Al_x(OH)_2(CO_3)_{x/2}.mH_2O \qquad (III);$$

$$(Ni_aMn_b)_{(1-x)}Al_x(OH)_2(A^{n-})_{x/n}.mH_2O \qquad (IV);$$

$$(Zn_aMn_b)_{(1-x)}Al_x(OH)_2(A^{n-})_{x/n}.mH_2O \qquad (V);$$

$$Co_{(1-x)}Al_x(OH)_2(CO_3)_{x/2}.mH_2O \qquad (VI);$$

$$(Co_{0.67}Mn_{0.33})_{(1-x)}Al_x(OH)_2(CO_3)_{x/2}.mH_2O \qquad (VII);$$

$$Co_{(1-x)}Fe_x(OH)_2(CO_3)_{x/2}.mH_2O \qquad (VIII),$$

wherein
$0.1 \leq x \leq 0.9$, preferentially $0.2 \leq x \leq 0.5$
$0.1 \leq a/b \leq 5$, preferentially $0.5 \leq a/b \leq 2$,
$A^{n-}$=anion of compensation, which may be carbonate, terephthalate or another anion, and
$m=n=1-(3/2)x+0.125$.

Preferentially, the said catalyst is based upon the reaction of niobium oxides with other metal oxides and obtained through the hydrothermal process, forming crystalline solids insoluble in aqueous solvents and ethylene glycol, comprising the general formula (IX), as follows:

$$Nb_xNa_{(x-y)}ZnO_x \qquad (IX),$$

wherein x, y and z=x=3 to 5.

In this manner, according to a preferential manner of embodiment, the process of obtainment of the catalysts according to the present invention comprises the following stages:

Catalysts Based Upon Hydrotalcites

Two series of precursors of hydrotalcite type were prepared utilizing sodium free raw materials, following the methodology employed by LIMA, Stevie Hallen, in Produção Direta de DME a Partir de Gás de Síntese em Sistema Catalítico Misto [Direct Production of DME from Synthesis Gas in Catalytic System], Institute of Chemistry, Federal University of Rio de Janeiro (IQ/UFRJ), 2014.

For the first series the starting point was the general formula $[(Zn)_{(i-x)}Al_x(OH)_2](CO_3)_{x/2}.mH_2O$, whilst for the other series the starting point was the general formula $(Zn_{0.53}Mn_{0.26})_{(1-x)}Al_x(OH)_2(CO_3)_{x/2}.mH_2O$. In both cases x was defined as 0.20. Preparation was carried out under conditions of a low degree of supersaturation by the method of coprecipitation at constant pH, commencing from a solution of the nitrates of the metals dissolved in 100 ml of water (denominated solution A), and another containing $(NH_4)_2CO_3$ and $NH_4OH$, in 100 ml of water (denominated solution B). Both were added dropwise, simultaneously, to 400 ml of water at a temperature of 65° C., under vigorous stirring, such that the pH was maintained at 6.5±0.3 during the addition. The precipitation times (of 0.5 to 2 h, preferentially 1 h) and of ageing (from 12 to 30 h, preferentially 20 h), were the same in all cases. Subsequently, the precipitates were washed and filtered with previously boiled water until the pH was neutral. Then, each solid obtained was dried at 100° C. for 4 h. The precursors were then calcined at a rate of 10° C. min$^{-1}$ from the ambient temperature to 350° C., whereat they remained for 3 h in order to obtain the mixed oxide.

The method of preparation of the mixed oxides catalysts based upon cobalt (CoAl, CoMnAl and CoFe) was similar to the method of synthesis of the ZnMnAl catalyst herein previously described, employing a variable pH (without pH control) or at a fixed pH controlled by means of the rate of addition of the solutions of metals and of $(NH_4)_2CO_3$ and $NH_4OH$. For these catalysts the pH (with or without control) lay in the range between 5 and 11, preferentially between 6 and 10.

Hydrotalcites of nickel (MII), manganese (MII) and aluminum (MIII) were also synthesized, varying the molar fraction $(X_{Al}^{+3})$ and utilizing sodium free or non-sodium free reagents, based upon the general formula of hydrotalcite type precursors, that is to say $[MII_{(1-x)}MIII_x(OH)_2]$ $(CO_3)_{x/2}.mH_2O$. For this purpose two mixed solutions were prepared, denominated A and B. Solution A was constituted by the nitrates of nickel and/or manganese and aluminum. Solution B was constituted by ammonium or sodium carbonate and ammonium or sodium hydroxide, respectively. All the reagents were dissolved in deionized water in a quantity sufficient for 100 ml. The synthesis vessel contained 400 ml of water and was monitored during the entire process by pH meter and thermometer. They were then added in a controlled manner to solutions A and B, maintaining the conditions of pH=6.5±0.3, temperature of 65±3° C. and stirring, until the exhaustion of the solutions, this taking on average from 30 to 60 minutes. Following this the system was maintained under stirring and at the same synthesis temperature during a period of between 2 and 7 hours, preferentially 4 hours, followed by ageing of the precipitate under stirring for a period of between 12 and 24 hours, preferentially 18 hours, and at the ambient temperature. Finally, the resulting suspension was filtered in a vacuum system and washed with approximately 1 l of boiling water in order to eliminate the nitrate ions. The filtrate was put to dry at 100° C., subsequently being crushed and calcined at 350° C. in a static air atmosphere.

In this document, when making reference to the catalysts/precursors, the nomenclature MII, MIII, X and $A^{n-}$ shall be adopted, wherein M is the metal of groups II and III, X the molar fraction of the trivalent metal and $A^{n-}$ is the anion of compensation, in this case being carbonate, having however two sources, that is to say $(NH_4)_2(CO_3)$, which shall be represented as $NH_4$, or $Na_2(CO_3)$, which shall be represented as Na. Consequently, the following precursor phases were prepared: $NiAl_{0.2}NH_4$, $NiAl_{0.5}NH_4$, $NiAl_{0.2}Na$, $NiAl_{0.5}Na$, $NiMn(1:2)Al_{0.2}NH_4$ and $NiMn(2:1)Al_{0.2}NH_4$. In the case of trivalent metals X is maintained constant and the proportion within brackets refers to the molar ratio of the metals.

Catalysts of Mixed Oxides Based Upon Niobium

Catalysts of oxide of zinc (ZnO) and niobium ($Nb_2O_5$—HY 340) were prepared in a basic medium (NaOH 10 M) at 180° C. under stirring at 120 rpm for 1 h. The solid obtained was then washed with water to completely remove the NaOH and dried in an oven. The quantity of ZnO in the formulation varied between 10 and 70%, preferentially between 20 and 60% of ZnO.

Process of Obtainment of Recycled Polyester (PET Depolymerization/Glycolysis)

The PET depolymerization reactions were carried out with recycled polyester (preferentially flakes of colorless PET bottles having a grain size of between 2 and 6 mm, preferentially 3 mm, obtained through milling at ambient temperature in a shredder 2, excess ethylene glycol 4 and the heterogeneous catalyst of interest 3, according to the present invention.

The PET depolymerization reactions were carried out utilizing 5 g of PET and 25 ml of ethylene glycol (EG), in the EG/PET molar proportion of 5/1, and 0.025 g of catalyst (0.5% by weight, considering the weight of PET) for the system of catalysts based upon Zn, Mn, Co and Al or 0.050 g of catalyst (1% by weight, considering the weight of PET) for the systems of catalysts containing nickel.

The heterogeneous catalysts tested in this reaction were previously rendered uniform in terms of the grain size thereof, the range of particle size of between 125 and 88 μm (170 to 120 Tyler mesh) being selected. In all cases the catalysts were calcined again under the same conditions as in the first calcination (rate of 10° C. min$^{-1}$ from the ambient temperature to 350° C., remaining at this temperature for 3 h), prior to each catalytic test (first utilization or reutilization), with the exception of the catalyst $Zn(Ac)_2$ employed as a reference.

Figure 13:
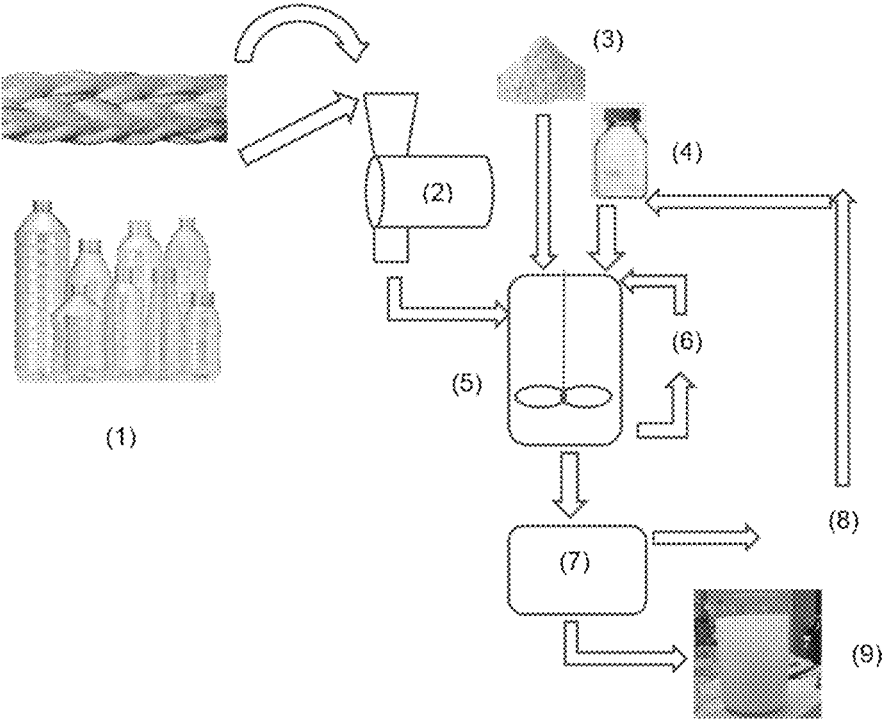
FIG. 13 represents a general schematic of the PET recycling process in accordance with the present invention.

Consequently, in accordance with a manner of embodiment of the invention (FIG. 13) the process of obtainment of recycled polyester, according to the present invention, comprises the following stages:

Optional milling of a mass of polyester 1 in a shredder 2;

Weighing a mass of polyester 1, of the catalyst 3 and of the ethylene glycol 4;

Addition of the mass of polyester 1, of the catalyst 3 and of the ethylene glycol 4 to the reactor 5 and over night contact;

Heating of the reaction mixture until the same enters reflux, calculating, from that point, the commencement of the reaction time for a period of between 30 min and 3 h, preferentially 1 h;

Filtration whilst hot (temperature>100° C.) of the solution obtained at the end of the period of reaction;

Drying the product retained at the ambient temperature and subsequently at a temperature of between 70 and 120° C., preferentially 80° C., until the completion of the drying, for a period of time of between 20 and 30 h, preferentially 24 h;

Following the cooling of the filtered solution to the ambient temperature, addition of water (approximately 0.2 I) to the product and, subsequently, filtration once more for the separation of the precipitated solid;

Subsequently, the filtered liquid was cooled 7 to a temperature of between −10° C. and 5° C., preferentially −5° C., over night, for crystallization of the BHET monomer, insoluble in cold water;

Filtration of the cooled liquid to separate the BHET monomer;

Drying of the BHET 9 retained at the ambient temperature for a period of time of between 20 and 30 h, preferentially 24 h, and subsequently at a temperature of between 70 and 120° C., preferentially 80° C., until the completion of the drying, for a period of time of between 20 and 30 h, preferentially 24 h;

Drying the solid materials, weighing and calculation of the yield from the reaction.

Optionally, the recycling 6 of the catalyst and the recycling 8 of the ethylene glycol.

Process of Obtainment of Recycled Polyester (PET Depolymerization/Glycolysis) in Parr Type Reactor The PET glycolysis experiments were carried out using a Parr reactor to evaluate conditions of better performance of the catalysts prepared in the obtainment of BHET having characteristics similar to those utilized in the PET production process utilized industrially.

The reaction conditions were the same as those aforedescribed, in duplicate, commencing however from a greater mass of PET and in conformity with the PET/CAT and PET/EG ratios employed in the previous experiments.

The PET conversion (%) and the molar yield of BHET (%) were determined by employing the following formulas:

$$\text{Conversão de } PET \ (\%) = \left( \frac{W_{PET,i} - W_{PET,f}}{W_{PET,i}} \right) * 100\%$$

$$\text{Rendimento molar } BHET \ (\%) = \left[ \frac{\left( \frac{W_{BHET,o}}{MW_{BHET}} \right)}{\left( \frac{W_{PET,i}}{MW_{PET}} \right)} \right] * 100\%$$

[key to Portuguese-language text in equations:

Conversão de PET=PET conversion

Rendimento molar BHET=BHET molar yield]

wherein $W_{(PET,i)}$ and $W_{(PET,f)}$ refer to the initial weight of PET and of final unreacted PET, respectively. $W_{(BHET,o)}$ refers to the total weight of BHET obtained, $MW_{PET}$ and $MW_{BHET}$, are the molar masses of PET (192 g mol$^{-1}$) and BHET (254 g mol$^{-1}$).

The description below shall be on the basis of preferential embodiments of the invention. As shall be evident to any person skilled in the art the invention is not limited to these particular embodiments.

EXAMPLES

Trials were carried out in order to illustrate the greater efficiency of the processes and of the catalysts according to the present invention, as described in the following examples:

Example 1: ZnAl Catalyst

Figure 2:
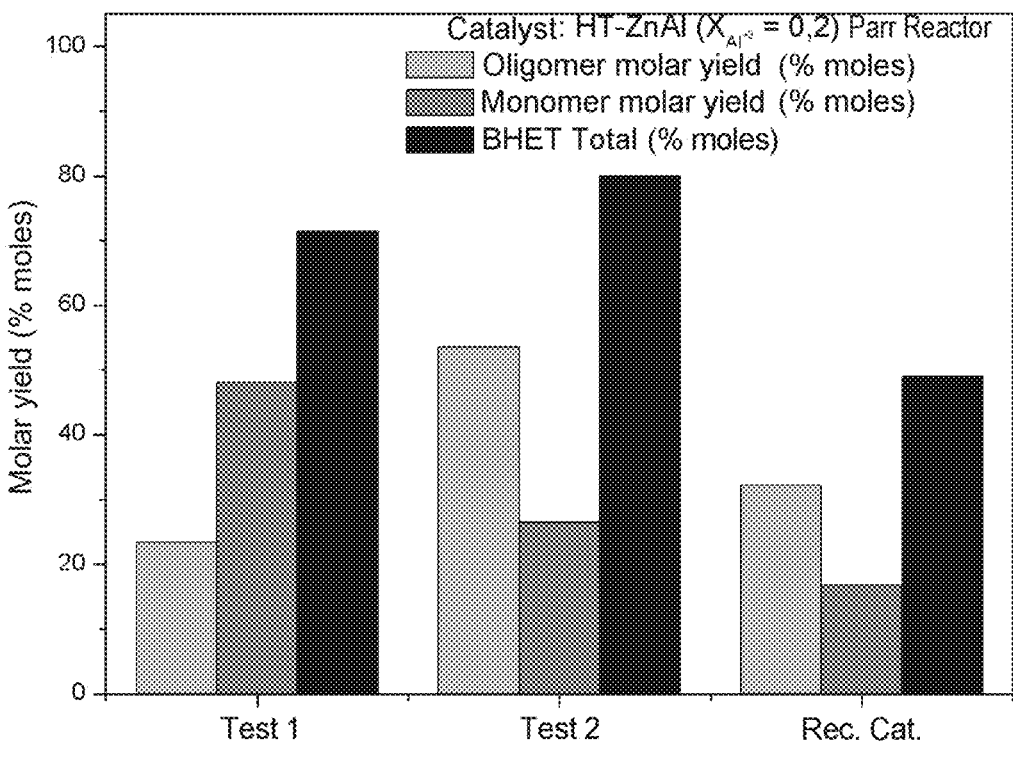
FIG. 2 represents the molar yield of BHET obtained from the depolymerization of PET with ZnAl oxide catalyst.

In FIG. 1 the results are shown of PET depolymerization carried out in the Parr reactor on a large scale for subsequent repolymerization. Good reproducibility is noted in respect of the batch tests (Tests 1 and 2) employing the mixed oxide catalyst originating from the hydrotalcite precursor phase HT-ZnAl. For the virgin mixed oxide (Tests 1 and 2) there was an average conversion of 99.7±0.1% after 1 h of reaction, starting from 40 g of PET (averages of Tests 1 and 2). For the Rec. Cat. system (PET conversion=76.89%) the same catalyst was used as used in Test 2, but recovered and utilized in another reaction without passing through any process of regeneration. Although it had not been regenerated, the catalyst still demonstrated that it was active in the depolymerization reaction in spite of exhibiting a drop of approximately 22% in the catalytic activity thereof. In FIG. 2 the results are shown of the molar yield of the tests of FIG. 1. The quantities obtained of BHET oligomer and monomer differ between Test 1 and Test 2 when compared with one another. However, when Test 2 is compared with the Rec. Cat., wherein the catalyst from Test 2 is reused, the molar yield decreases by a proportion approximating to the conversion (ca. 38% decrease).

Example 2: ZnMnAl Catalyst for Glycolysis of PET and of Fibres from Polyester Ropes In FIG. 3 the graphs are shown of conversion of PET into BHET for the catalyst of the mixed oxide type obtained from the HT-ZnMnAl precursor phase, with the incorporation of manganese in the structure of the ZnAl. The virgin mixed oxide, and the reutilized oxide (Rec. Cat.) presented practically the same conversion. It is important to highlight that, in this case, the catalyst recovered from Test 1 was utilized in a further PET depolymerization reaction, however without heat treatment of drying and calcination and in conformity with the same PET/CAT proportion. It may be observed that the result of conversion of PET into BHET was perfectly reproduced (100% in Test 1 and 99.9% in the Rec. Cat.) when the result from the reutilized catalyst is compared with the result from the virgin catalyst (Test 1). It is important to highlight that, following carrying out Test 1, the catalyst retained on the filter paper was transferred to a controlled humidity desiccator and, prior to carrying out the further test, a thermogravimetric analysis (TGA) experiment was carried out under an atmosphere of $N_2$, having the objective of obtaining the weight of catalyst recovered free of physically absorbed EG and/or BHET mixed with the catalyst. Consequently, the PET/CAT ratio used in the new test was in conformity with the weight of catalyst recovered free of humidity, of physically adsorbed EG and/or admixed BHET.

Figure 3:
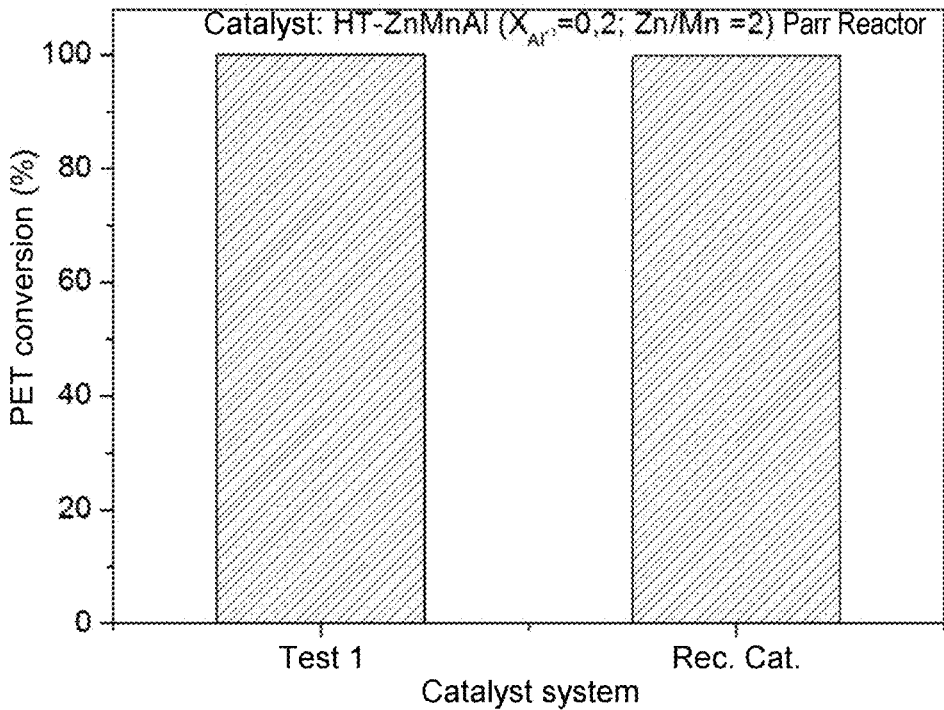
FIG. 3 represents the conversion of PET into BHET with ZnMnAl oxide catalyst.
Figure 4:
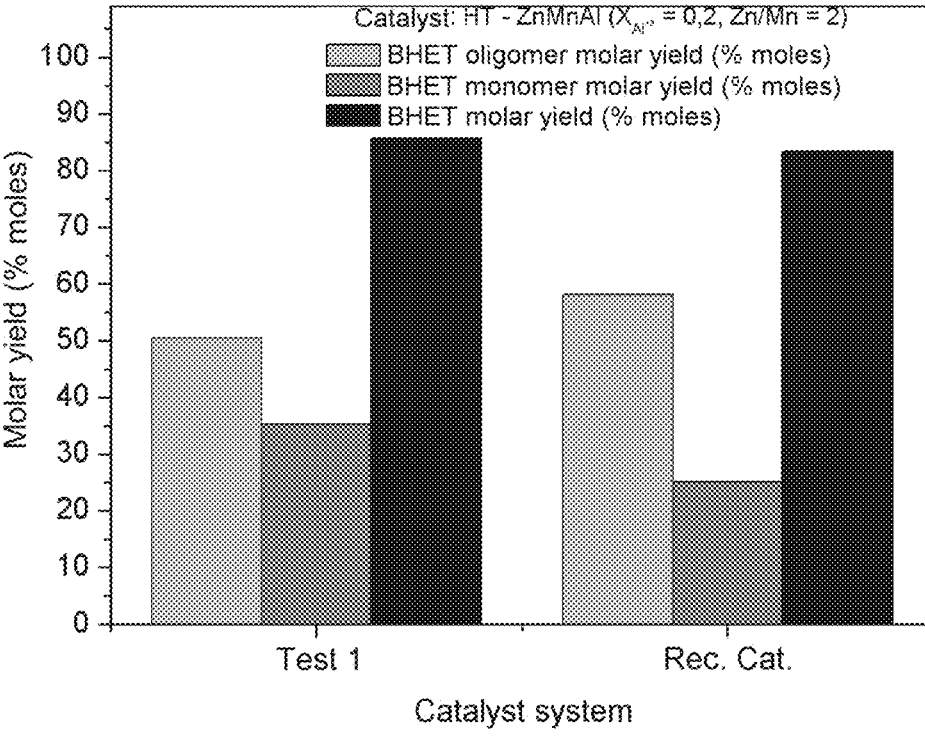
FIG. 4 represents the molar yield of BHET obtained from the depolymerization of PET with ZnMnAl oxide catalyst.

In FIG. 4 the results are shown of the molar yield in BHET from the PET depolymerization test of FIG. 3. Good reproducibility of the molar yield result was found with the recycled catalyst (Rec. Cat.), corroborating the belief that the catalyst obtained from the HT-ZnMnAl system did not suffer modifications to the structure thereof such as to affect the catalytic performance thereof. Consequently, under the batch reaction conditions (80 g of PET, 400 ml of EG, 200° C., 500 rpm, 17 psi and 1 h of reaction) the catalyst demonstrated good thermal and mechanical stability.

TABLE 1

| PET conversion kinetics for the catalysts ZnMnAl and ZnAl | | | | | |
|---|---|---|---|---|---|
| Catalyst/ Conversion | 1 min | 5 min | 10 min | 15 min | 60 min |
| ZnAl | 2 | 8 | 19 | 30 | 50 |
| ZnMnAl | 4 | 6 | 26 | 96 | 97 |

Table 1 shows the results of conversion of polyester ropes used for mooring petroleum production platforms. The results show that in 60 minutes the conversion by the catalyst ZnAl for glycolysis of the polyester was only 50% against 98.5% conversion in the glycolysis of flakes of PET (FIG. 1). This result shows the difficulty in promoting the glycolysis of ropes of polyester fibres in comparison with flakes from PET bottles. As is known in the literature, the ropes originate from industrial fibre grade PET. This material differs considerably from the textile fibre grade and the bottle grade by virtue of the fact that it possesses a viscosity index (V.I.) exceeding that of the bottle grades of the order of 1.0. This signifies that the PET from the ropes possesses a greater molar mass. The acceptable V.I. range in these grades is very considerably narrower, that is to say that the polymer molecules are uniformly larger. In addition, industrial fibre grade PET is not produced with the addition of comonomers, this resulting in the polymer being more crystalline. By virtue of not being produced with additives, the recycling of the ropes experiences less interference from additives, being of greater interest in terms of the use of the BHET returning to the industrial process.

Continuing the analysis of Table 1, it may be observed that the conversion of polyester fibres with the catalyst ZnMnAl was of 97% in 60 minutes of reaction. This result shows a strong synergy between the manganese and the zinc and aluminium. This synergy continues to be evident when the catalysts ZnMnAl and ZnAl are compared in terms of the conversion kinetics of the fibre in different reaction times. The results show that in solely 15 minutes of reaction the conversion from the catalyst ZnMnAl was of 96%, whilst from the catalyst ZnAl it was only 30%. The conversion approaching 100% in 15 minutes is a very important result to decrease the cost of the process, by virtue of the fact that it will require less reaction time and a smaller size of the depolymerization reactor.

In spite of the fibres being more crystalline than the bottles, both the heterogenous catalyst ZnMnAl was effective in the depolymerization thereof. The literature does not provide any result on glycolysis of polyester fibres, confirming the novelty of these results.

Example 3: NiAl and NiMnAl Oxide Catalyst for PET Glycolysis

Figure 5:
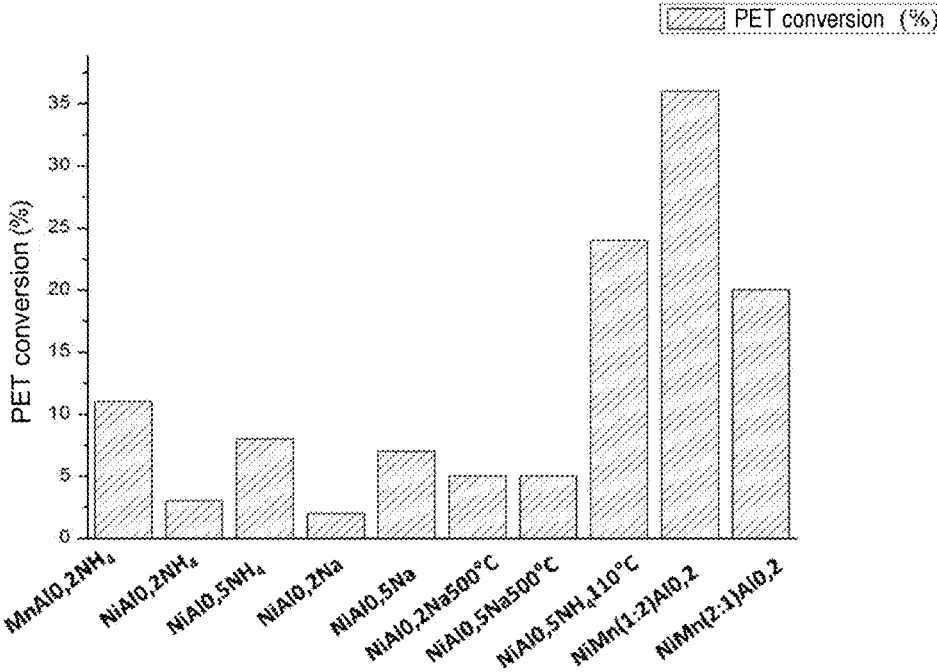
FIG. 5 represents the conversions of PET from the oxide catalysts obtained from hydrotalcites of Ni, Al and Mn.

To a reaction vessel of perfluoroalcoixide wrapped in a metal blanket there were added 25 ml of ethylene glycol, 5 g of PET and 25 mg of the catalyst previously calcined at a rate of 10° C. $min^{-1}$ from the ambient temperature to 350° C., being held at this temperature for 3 h. This system was held for 18 hours at ambient temperature for the purpose of the prior and prolonged contact of the reagents. Following this, the reaction vessel was subjected to heating at a rate of 20° C. $min^{-1}$ to 200° C., being held at the final temperature for 1 hour under mechanical stirring and autogenous pressure. The conditions listed were achieved utilizing a Mars Synthesis 6 model microwave reactor from CEM Corporation having temperature control and pressure readout. This stage was divided into two phases: Firstly, the phase of screening trials of Ni catalysts, having the objective of optimizing and detecting the catalyst presenting greatest conversion. The second phase was a study of the factors influencing the yield from the best catalyst. In this second phase modifications were made to the methodology of the catalytic test. Instead of the microwave reactor, a mantle heated round bottomed flask was utilised, magnetically stirred and under reflux. In addition, to ensure the greatest recovery of BHET monomer, the filtrate from the 1$^{st}$ filtration was washed with boiling water, by virtue of the fact that the catalyst is not soluble in water. The advantage was confirmed through a prior test. Following the reaction, the filtered materials were dried to obtain the PET conversions, as listed in FIG. 5. It may be concluded that the best catalyst from among those tested was NiMn(1:2)Al$_{0.2}$NH$_4$. There is an increase in the conversion of PET with greater proportions of Mn when combined with Ni (Ni/Mn=½). The concurrence of Ni and Mn showed greater activity when compared with the catalysts containing these metals alone. An increase of 5 and 3 times, respectively, is noted, revealing a clear synergy between these metals for the conversion of the PET. The calcination temperature of 500° C. showed a reduction in the catalytic activity, possibly due to the sintering effect. A further relevant aspect was the 4 times greater conversion of the precursor catalyst NiAl$_5$NH$_4$ when this was not calcined, solely dried at 110° C., as was realized with all the other precursors.

Figure 6:
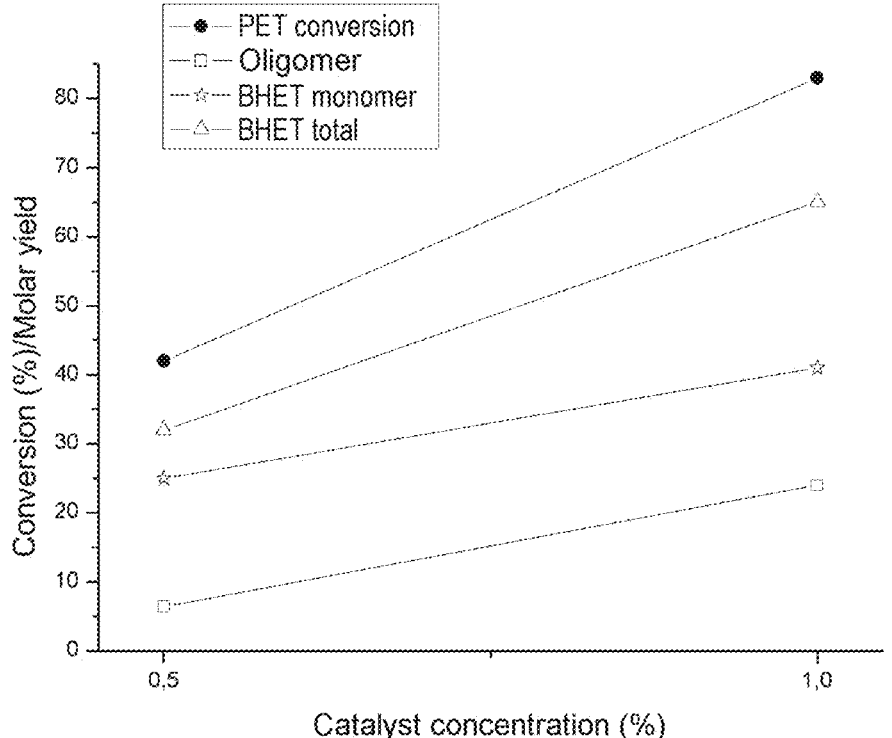
FIG. 6 represents the results of conversions of PET and molar yield (oligomer, monomer and total BHET) as a function of the concentration of the catalyst in relation to the weight of PET.
Figures 7, 8:
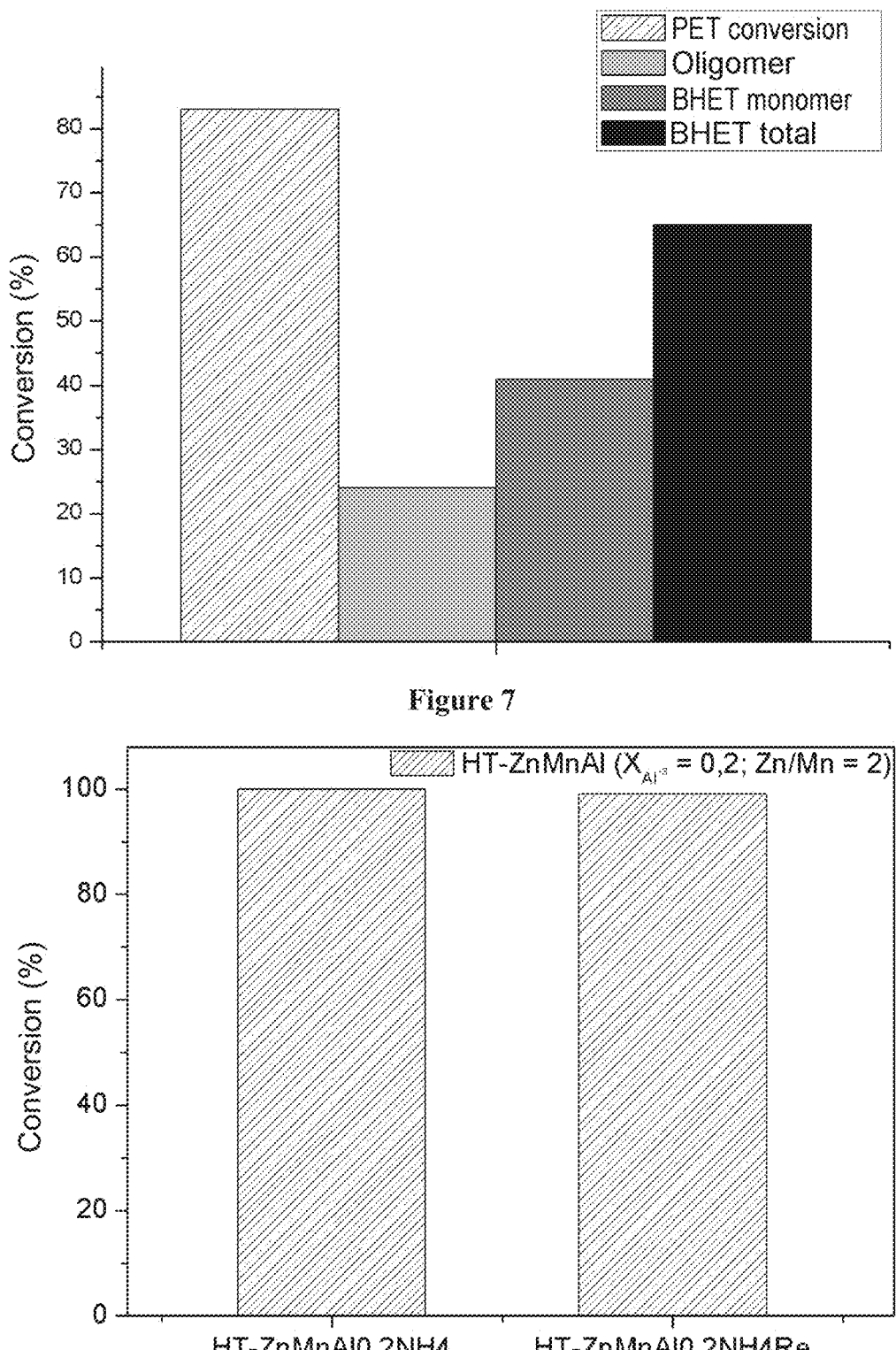
FIG. 7 represents the results of conversions of PET and molar yield (%) of the products for 1% of $NiMn1:2Al_{0.2}NH_4$ oxide catalyst with reference to the weight of PET.
FIG. 8 represents the conversion of ropes of polyester into BHET with ZnMnAl oxide catalyst ("Re"=repetition of the experiment).

The catalyst having the greatest catalytic activity was applied in a higher concentration in relation to the weight of PET and it exhibited double the conversion, achieving 81% PET conversion, as shown in FIG. 6. The total molar yield of BHET attained values of 60%, it being noted that the catalyst is more selective for the monomer in detriment to the oligomer. The concentrations in FIG. 6 are shown in weight percentage, wherein 0.5% corresponds to 25 mg of catalyst/5 g of PET, and 1% corresponds to 50 mg of catalyst/5 g of PET. In FIG. 7 there are shown in greater detail the conversion of PET and molar yields of the products for the case wherein 1.0% of catalyst was used. It is noted that this catalytic system has a greater tendency towards BHET monomer rather than oligomer conversion.

Example 4: Details of Recycling Fibres from Polyester Ropes with the Catalyst ZnMnAl$_{0.2}$NH$_4$ 10 g of fibers of post user polyester originating from an offshore application together with 50 ml of ethylene glycol and 50 mg of calcined catalyst (ZnMnAl$_{0.2}$NH$_4$) were placed in a 1 l flask having a reflux system. All the components were held in contact previously for 18 h prior to the depolymerization reaction. Subsequently, the system was heated to 196° C., whereat it remained for 60 min. Following this period all the fiber was depolymerized into BHET and was then filtered whilst still hot for the purpose of separation from the catalyst. In FIG. 8 the results are shown of conversion, undertaken in duplicate, of the post user polyester fibers into BHET. In both cases the conversion was of approximately 100%.

Figure 9:
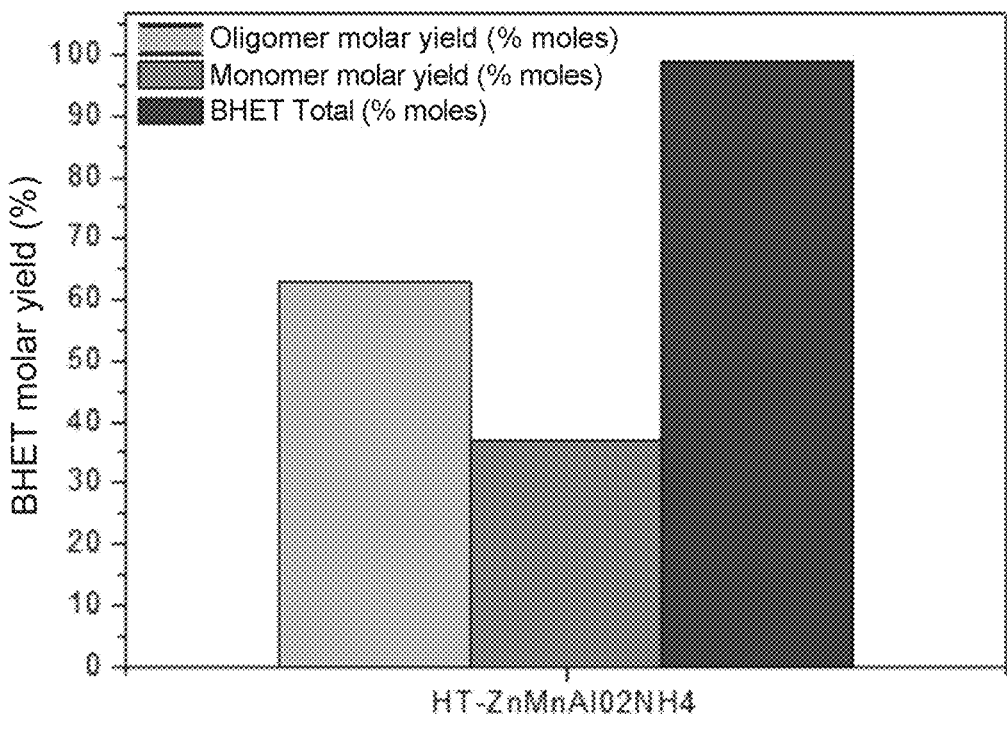
FIG. 9 represents the molar yield of the products originating from the depolymerization of polyester ropes, obtained with the ZnMnAl oxide catalyst.

In FIG. 9 the results are shown of the molar yield of the BHET oligomer and BHET monomer products, and greater selectivity is noted for the oligomeric fraction.

Example 5: Preparation of the Mixed Oxide Catalyst of Niobium and Zinc

To an autoclave reactor clad internally by a teflon liner there were added 180 ml of an aqueous solution of NaOH 10 M, 2.7 g of oxide niobium, Nb$_2$O$_5$ (HY 340), and 0.6 g of zinc oxide (ZnO). The components of the reaction were heated to 180° C. and the reaction system was held under stirring at 120 rpm for 1 h. Following the end of the period of reaction the heating was switched off, permitting the temperature to slowly reach the ambient temperature. The solid obtained was then subjected to 4 washings with water for the complete removal of the NaOH, in each washing it being subjected to centrifuging at 2000 rpm for the separation of the product. Following oven drying, a solid in the form of fibrous crystals (catalyst 20% ZnONb$_2$O$_5$) was obtained. The same methodology was utilized to produce two further catalysts, modifying solely the quantity of ZnO in the formulation, being of 1.2 and 2.4 g, producing the catalysts 40% ZnONb$_2$O$_5$ and 60% ZnONb$_2$O$_5$, respectively.

Example 6: PET Recycling with Catalysts Based Upon Niobium

Approximately 5 g of PET originating from bottles in the form of flakes were placed in contact with 25 ml of ethylene glycol (EG) in the EG/PET molar proportion of 5/1 and 0.025 g of catalyst having a needles morphology of the sodium and zinc niobate type (0.5% by weight, considering the weight of PET). The dispersion was allowed to stand for approximately 16 h. Following this period of contact the system was heated to reflux, commencing the calculation of the time of 3 h. This period of glycolysis having been completed, the material was subjected to a filtration, there then being added 200 ml of water to the filtered liquid, forming a precipitate. The precipitated product was filtered, the material passing through the filter being collected and placed in a freezer wherein it remained for 12 h. After this period, the material was removed from the freezer and filtered for a third time. The solid products retained on the filters were dried, collected and weighed and analyzed by X-ray diffraction (XRD) and DSC. The same procedure was undertaken utilizing niobic acid (hydrated niobium oxide) heat treated (calcined) at different temperatures, as homogenous catalyst. The conversions into BHET and oligomeric product are shown in Table 2. The niobates possessing a morphology in the form of fibers presented yields greater than those obtained by means of niobic acid calcined at diverse temperatures, with conversions of up to 95% total conversion, against 60% with the best catalyst based upon niobic acid.

TABLE 2

| PET depolymerization reactions | | |
|---|---|---|
| | Conversion (%) | |
| Catalyst | Oligomer | BHET |
| 20% ZnO Nb$_2$O$_5$ | — | 85.6 |
| Na$_2$O Nb$_2$O$_5$ | 5.21 | 89.8 |
| 20% ZnO Nb$_2$O$_5$ | 0.82 | 87.3 |
| 40% ZnO Nb$_2$O$_5$ | — | 65.3 |
| 60% ZnO Nb$_2$O$_5$ | 83.6 | 16.2 |
| ZnO | 1.04 | 33.6 |
| Niobic acid HY340 | — | 67.0 |
| Niobic acid HY340 (300° C. for 6 h) | 1.57 | 58.6 |
| Niobic acid HY340 (400° C. for 6 h) | 15.8 | 45.0 |
| Niobic acid HY340 (500° C. for 6 h) | 13.4 | 15.1 |
| Niobic acid HY340 (600° C. for 6 h) | — | 44.0 |

Figure 10:
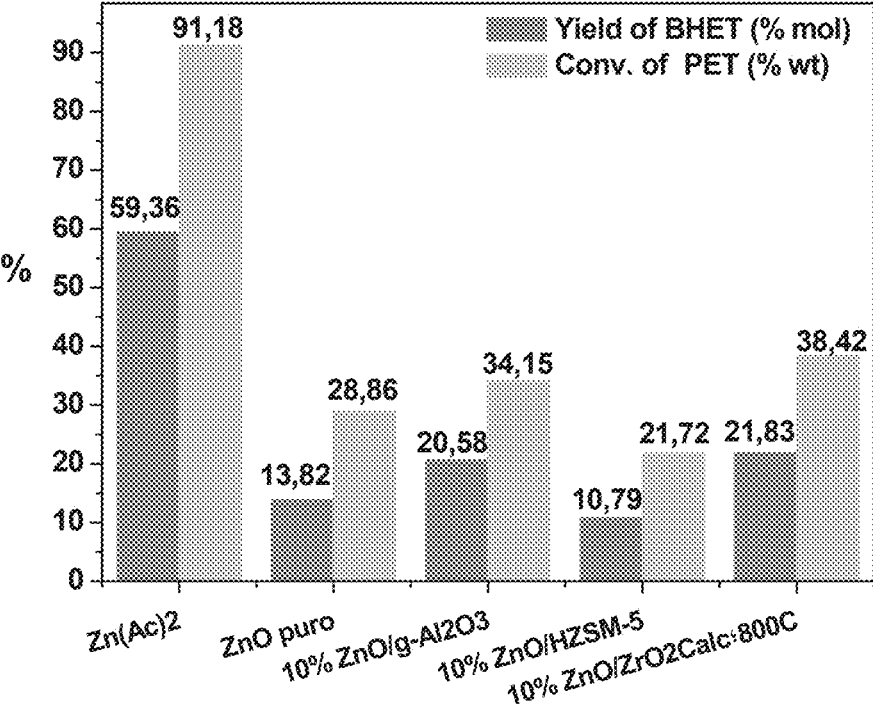
FIG. 10 represents the conversion of PET (% wt) and yield of BHET (% mol) for the diverse catalysts tested based upon zinc.

Comparative tests of the depolymerization of PET were also carried out with homogenous catalyst of zinc acetate (Zn(Ac)$_2$), with pure zinc oxide (ZnO) and with catalysts based upon zeolites, alumina and zirconia impregnated with ZnO (ZnO/Al$_2$O$_3$, ZnO/HZSM and ZnO/ZrO$_2$, respectively). The results are shown in FIG. 10.

Figure 11:
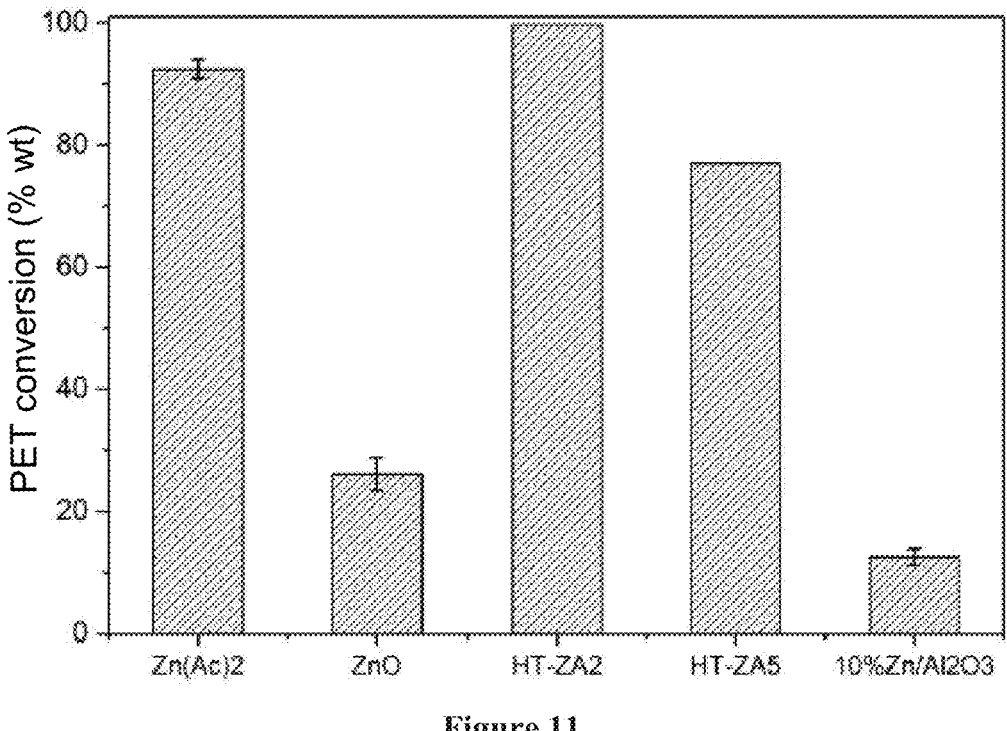
FIG. 11 represents the conversion of PET (w/w) for the other systems containing Zn.
Figure 12:
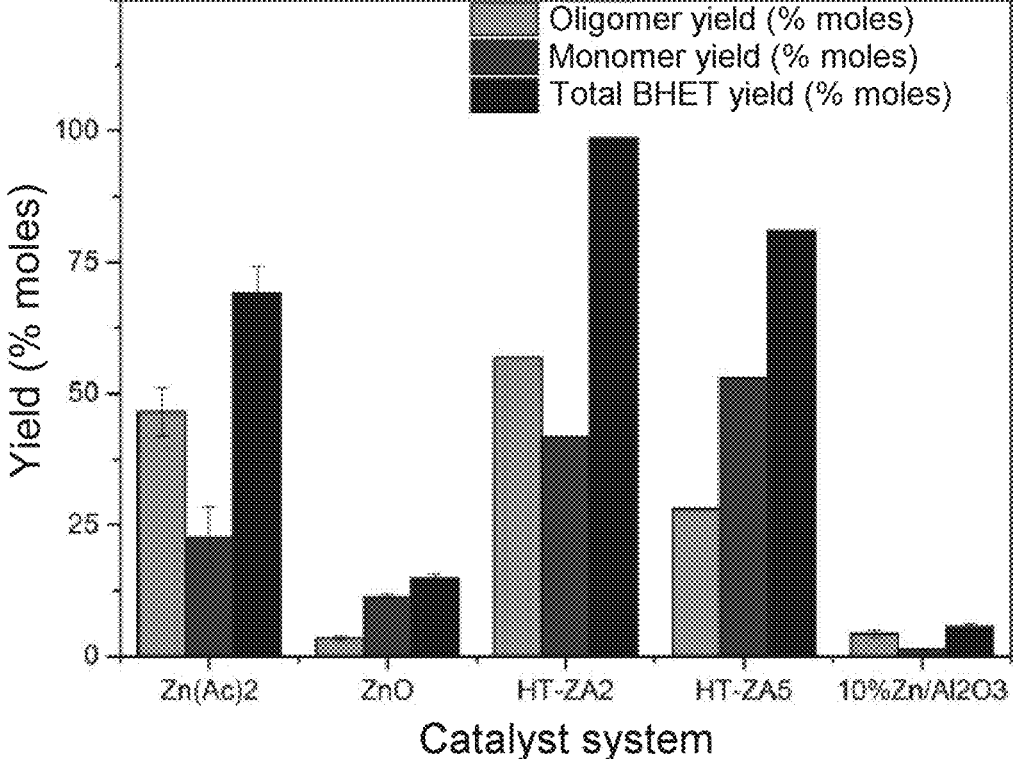
FIG. 12 represents the distribution of products (% mol) for the catalytic systems containing Zn.

Similarly, depolymerization tests employing catalysts based upon alumina and hydrotalcites were carried out and compared with the depolymerization with ZnO. The results are shown in FIGS. 11 and 12.

Example 7: Recycling of Fibers from Polyester Ropes with the Catalyst 40% $ZnONb_2O_5$ Approximately 5 g of PET fibers originating from post user ropes arising from offshore application, 0.025 g of the catalyst 40% $ZnONb_2O_5$ and 70 ml of ethylene glycol were placed in a glass reactor wherein they were held in contact for approximately 12 h. Subsequent to this period in contact the system was heated until entering reflux, commencing the calculation of the period of reaction of glycolysis. The reaction was continued until all the fiber had been totally consumed. Having completed the depolymerization stage, the material was subjected to a first filtration, 200 ml of distilled water then being added to the filtered liquid. The precipitated material was then filtered a second time, the material passing through the filter being collected and placed in a freezer wherein it remained for 12 h., This period having elapsed, the material was removed from the freezer and filtered for a third time. The solid products retained on the filters were dried, collected and weighed and analyzed by X-ray (XRD). The same procedure was carried out utilizing zinc acetate $(Zn(Ac)_2)$ as homogenous catalyst. A conversion of 62% was obtained for the reaction undertaken with the catalyst 40% $ZnONb_2O_5$, whilst the homogenous catalyst presented a conversion of 54%. This result of 62% conversion with the heterogeneous catalyst 40% $ZnONb_2O_5$ may be significantly improved through the increase in the weight of catalyst.

The present invention presents examples demonstrating the excellent activity of these catalysts in the recycling of the ropes by glycolysis with ethylene glycol, which cannot be anticipated, considering that the morphology of the polyester fibers presents differences in terms of characteristics in relation to the morphology of the bottles.

As is known, the ropes originate from industrial fiber grade PET. This material differs considerably from the textile fiber grade and from the bottle grade by virtue of the fact that it possesses an intrinsic viscosity (VI) greater than the fiber and bottle grades (in the order of 1.0). This signifies that the PET from the ropes possesses a greater molar mass. The acceptable V.I. range of these grades is very considerably narrower, that is to say that the polymer molecules are uniformly larger. In addition, industrial fiber grade PET is not produced with the addition of comonomers, this resulting in the polymer being more crystalline. By virtue of not being produced with additives, the recycling of the ropes experiences less interference from additives, being of greater interest in terms of the use of the BHET returning to the processing medium (see below). In spite of the fibers being more crystalline than the bottles, both the heterogeneous catalysts were effective in the depolymerization thereof.

It must furthermore be highlighted that the fibers of the used ropes presented encrustations originating from exposure thereof to the sea water for long periods, which could result in interference in the performance of the catalyst employed. However, in the example presented, the catalysts employed maintained their high efficiency, even under these conditions.

Example 8: Mixed Oxide Catalysts of CoAl, CoMnAl and CoFe for PET Glycolysis Mixed oxide catalysts of CoAl, CoMnAl and CoFe were prepared from the calcination of hydrotalcites having the following formulas:

$Co_{0.8}Al_{0.2}(OH)_2(CO_3^{2-})_{0.1}.mH_2O$, for the CoAl catalysts (variable pH and fixed pH=6.6);

$Co_{0.54}Mn_{0.26}Al_{0.2}(OH)_2(CO_3^2)_{0.1}.mH_2O$, for the CoMnAl catalysts (variable pH and fixed pH=6.6);

$Co_{0.8}Fe_{0.2}(OH)_2(CO_3^2)_{0.1}.mH_2O$, for the CoFe catalysts (variable pH and fixed pH=10), wherein x=0.20 and m=1–(3/2)x+0.125.

The variable pH (without pH control) or the fixed pH were controlled by the rate of addition of the solutions of metals and of $(NH_4)_2CO_3$ and $NH_4OH$.

In the depolymerization test a reflux reactor was used constituted by a flask having two necks connected to a condenser (to provide the reflux of the ethylene glycol), a thermocouple and a heating mantle. 25 ml of ethylene glycol, 5 g of PET flakes originating from bottles and 0.025 g of catalyst were added to the reactor. Initially, a period of contact between the reagents and the catalyst at ambient temperature was established at 18 hours. The reaction vessel was then subjected to heating at a rate of 20° C. min$^{-1}$ to 200° C., under mechanical stirring and a pressure of 1.01× $10^{-5}$ Pa (1 atm). The reagents remained heated for 60 minutes at the final temperature of 200° C. Catalyst screening tests provided the comparison between the catalysts synthesised through the conversion and the yield of products.

Figure 14:
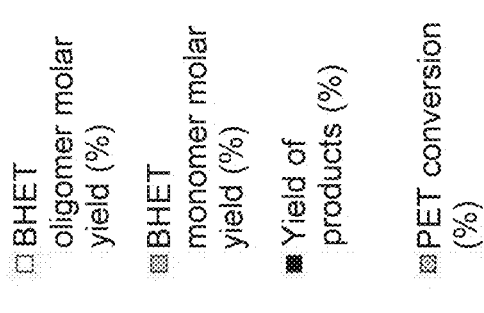
FIG. 14 represents the conversion of PET, molar yield of BHET monomer, molar yield of BHET oligomer and molar yield of products (BHET monomer+oligomer) in the tests with the catalysts based upon cobalt.

FIG. 14 shows that the catalyst $CoAl_{(variable\ pH)}$ presented a 40.2% conversion of PET, whilst the CoAl synthesised with pH controlled at 6.6 presented a greater conversion, being of 57.6%. The introduction of the Mn into the CoMnAl$_{(variable\ pH)}$ catalyst led to an increase in the conversion to 97.5%. The catalyst CoFe(variable pH) resulted in a conversion of 70%, whilst the CoFe$_{(pH\ 10)}$ resulted in a conversion of 95.9%.

The description set out herein of the object of the present invention shall be considered solely as one embodiment or possible embodiments and any particular characteristics introduced thereinto shall be understood solely as a matter which has been included to facilitate the comprehension. In this manner, they cannot be deemed to limit whatsoever the invention, it being limited to the scope of the claims hereinafter.

The invention claimed is:

1. A catalyst for the obtainment of recycled polyester, comprising the following general formulas:

$$(Zn_{0.67}Mn_{0.33})_{(1-x)}Al_x(OH)_2(CO_3)_{x/2}.mH_2O \qquad (II);$$

$$(Ni_aMn_b)_{(1-x)}Al_x(OH)_2(A^{n-})_{x/n}.mH_2O \qquad (IV);$$

$$(Zn_aMn_b)_{(1-x)}Al_x(OH)_2(A^{n-})_{x/n}.mH_2O \qquad (V);\ and$$

$$(Co_{0.67}Mn_{0.33})_{(1-x)}Al_x(OH)_2(CO_3)_{x/2}.mH_2O \qquad (VII),$$

wherein $0.2 \leq x \leq 0.5$, $0.1 \leq a/b \leq 5$, $A^{n-}$=anion of compensation, which may be carbonate, terephthalate or another anion, and $m=1–(3/2)x+0.125$.

2. The catalyst of claim 1, the catalyst having the following general formula:

$$(Co_{0.67}Mn_{0.33})_{(1-x)}Al_x(OH)_2(CO_3)_{x/2}.mH_2O \qquad (VII),$$

wherein x=0.20 and m=1–(3/2)x+0.125.

3. A catalyst for the obtainment of recycled polyester, the catalyst consisting essentially of one of the following general formulas:

$$(Zn_{0.67}Mn_{0.33})_{(1-x)}Al_x(OH)_2(CO_3)_{x/2}.mH_2O \qquad (II);$$

$$(Ni_aMn_b)_{(1-x)}Al_x(OH)_2(A^{n-})_{x/n}.mH_2O \qquad (IV);$$

$$(Zn_aMn_b)_{(1-x)}Al_x(OH)_2(A^{n-})_{x/n}.mH_2O \qquad (V);\ and$$

$$(Co_{0.67}Mn_{0.33})_{(1-x)}Al_x(OH)_2(CO_3)_{x/2}.mH_2O \qquad (VII),$$

wherein $0.2 \leq x \leq 0.5$, $0.1 \leq a/b \leq 5$, $A^{n-}$=anion of compensation, which may be carbonate, terephthalate or another anion, and $m = 1 - (3/2)x + 0.125$.

* * * * *